US012564700B2

(12) United States Patent
Ilaria et al.

(10) Patent No.: US 12,564,700 B2
(45) Date of Patent: Mar. 3, 2026

(54) DEVICE FOR INDUCING ALTERNATING TACTILE STIMULATIONS

(71) Applicant: BLS Remote LLC, New York, NY (US)

(72) Inventors: Gerard R. Ilaria, New York, NY (US); Dustin D. Shryock, New York, NY (US)

(73) Assignee: BLS Remote LLC, New York, NY (US)

( * ) Notice: Subject to any disclaimer, the term of this patent is extended or adjusted under 35 U.S.C. 154(b) by 941 days.

(21) Appl. No.: 17/493,459

(22) Filed: Oct. 4, 2021

(65) Prior Publication Data

US 2022/0105309 A1      Apr. 7, 2022

Related U.S. Application Data

(60) Provisional application No. 63/086,879, filed on Oct. 2, 2020.

(51) Int. Cl.
A61M 21/02          (2006.01)
A61M 21/00          (2006.01)

(52) U.S. Cl.
CPC ..... A61M 21/02 (2013.01); *A61M 2021/0022* (2013.01); *A61M 2021/0027* (2013.01); *A61M 2021/0044* (2013.01); *A61M 2205/3553* (2013.01)

(58) Field of Classification Search
CPC .......... A61M 21/02; A61M 2021/0022; A61M 2021/0027; A61M 2021/0044; A61M 2205/3553; A61M 2205/3592; A61M 2205/60

USPC ...................................................... 600/26–28
See application file for complete search history.

(56) References Cited

U.S. PATENT DOCUMENTS

| | | | |
|---|---|---|---|
| 6,001,073 A | 12/1999 | Schmidt et al. ................ 601/72 |
| 2004/0161730 A1* | 8/2004 | Urman ................... G09B 19/00 |
| | | | 434/236 |
| 2005/0171411 A1* | 8/2005 | KenKnight ............ G16H 40/63 |
| | | | 600/300 |
| 2010/0323335 A1* | 12/2010 | Lee .......................... A61B 5/16 |
| | | | 434/236 |

(Continued)

*Primary Examiner* — Sunita Reddy
(74) *Attorney, Agent, or Firm* — Stein IP LLC

(57)          ABSTRACT

A system for providing a therapy session between a therapist and a patient includes a therapist interface device that is configured for presenting a therapist user at a first location with a control interface to communicate with a remote patient interface device at a second location. The patient interface device is configured for presenting a patient user with a communication interface for communicating with the therapist interface device over a network. A stimulation device is located at the second location with the patient interface device and to provide tactile stimulation to a patient user, such as bilateral tactile stimulation. The stimulation device is coupled with the patient interface device for receiving stimulation instructions from the patient interface device. The control interface of the therapist device receives a control input from the therapist user and uses the control input to generate stimulation instructions to drive the stimulation device to provide tactile stimulation to the patient user based upon the control input

8 Claims, 8 Drawing Sheets

(56) References Cited

U.S. PATENT DOCUMENTS

| | | | | |
|---|---|---|---|---|
| 2014/0081661 A1* | 3/2014 | Fu | .......................... | G16H 20/30 |
| | | | | 705/3 |
| 2017/0296775 A1* | 10/2017 | Mayo | ..................... | G16H 20/70 |
| 2018/0318545 A1* | 11/2018 | Jones | .................... | A61M 21/02 |
| 2020/0086077 A1* | 3/2020 | Gazit | .................... | A61M 21/02 |
| 2020/0261688 A1* | 8/2020 | Thoma | ................. | A61M 21/02 |
| 2020/0376230 A1* | 12/2020 | Causey | ................. | A61M 21/02 |
| 2021/0213239 A1* | 7/2021 | Jones | .................... | A61M 21/02 |
| 2021/0353904 A1* | 11/2021 | Hanbury | ............... | A61M 21/02 |
| 2021/0401194 A1* | 12/2021 | Johancen | ............. | A61B 5/4848 |
| 2022/0088344 A1* | 3/2022 | Pape | ..................... | A61M 21/00 |
| 2022/0105309 A1* | 4/2022 | Ilaria | ................... | A61M 21/02 |
| 2023/0337952 A1* | 10/2023 | Emma | .................. | A61M 21/00 |

* cited by examiner

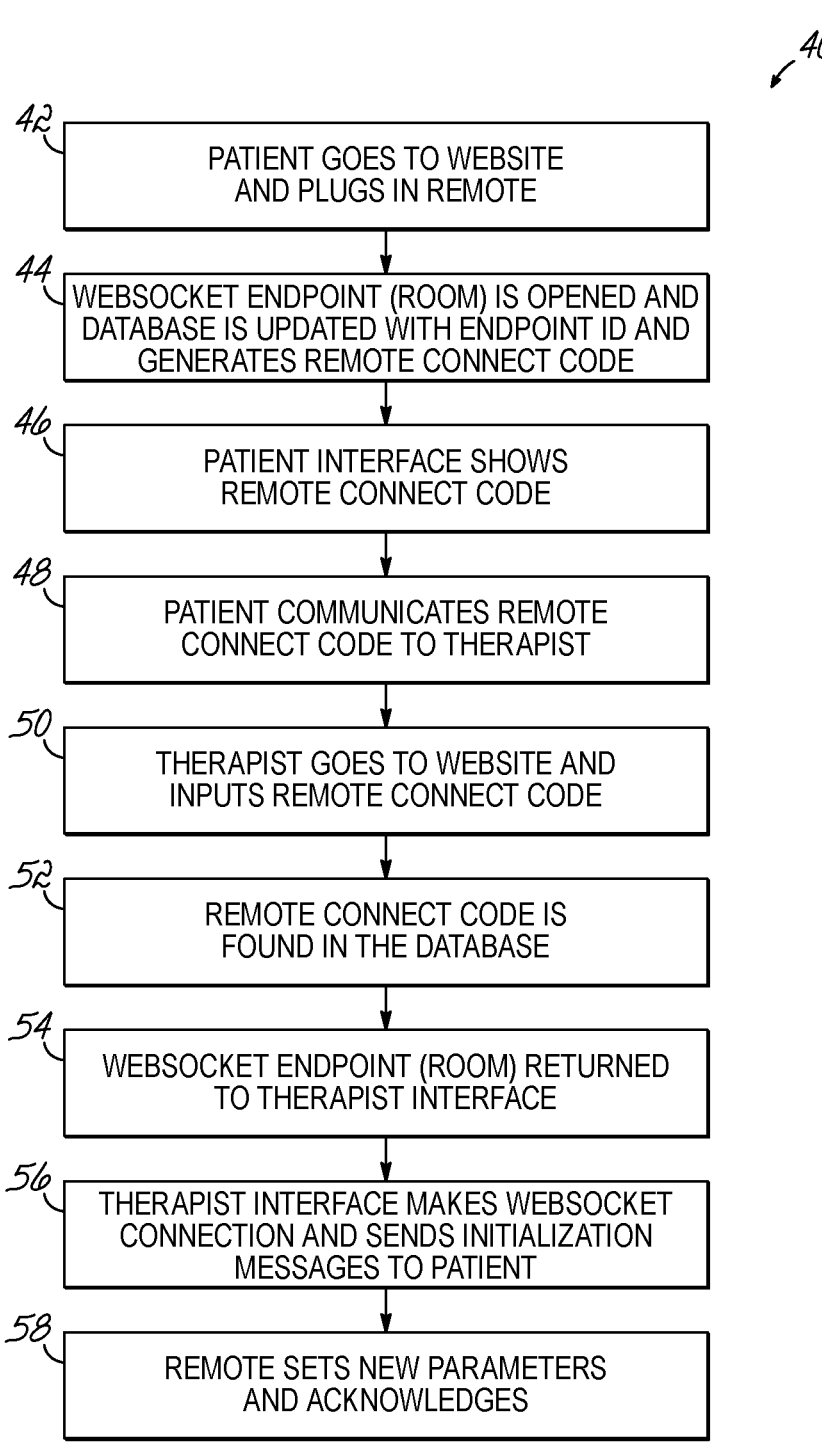

*40*

*42* PATIENT GOES TO WEBSITE
AND PLUGS IN REMOTE

*44* WEBSOCKET ENDPOINT (ROOM) IS OPENED AND
DATABASE IS UPDATED WITH ENDPOINT ID AND
GENERATES REMOTE CONNECT CODE

*46* PATIENT INTERFACE SHOWS
REMOTE CONNECT CODE

*48* PATIENT COMMUNICATES REMOTE
CONNECT CODE TO THERAPIST

*50* THERAPIST GOES TO WEBSITE AND
INPUTS REMOTE CONNECT CODE

*52* REMOTE CONNECT CODE IS
FOUND IN THE DATABASE

*54* WEBSOCKET ENDPOINT (ROOM) RETURNED
TO THERAPIST INTERFACE

*56* THERAPIST INTERFACE MAKES WEBSOCKET
CONNECTION AND SENDS INITIALIZATION
MESSAGES TO PATIENT

*58* REMOTE SETS NEW PARAMETERS
AND ACKNOWLEDGES

FIG. 2

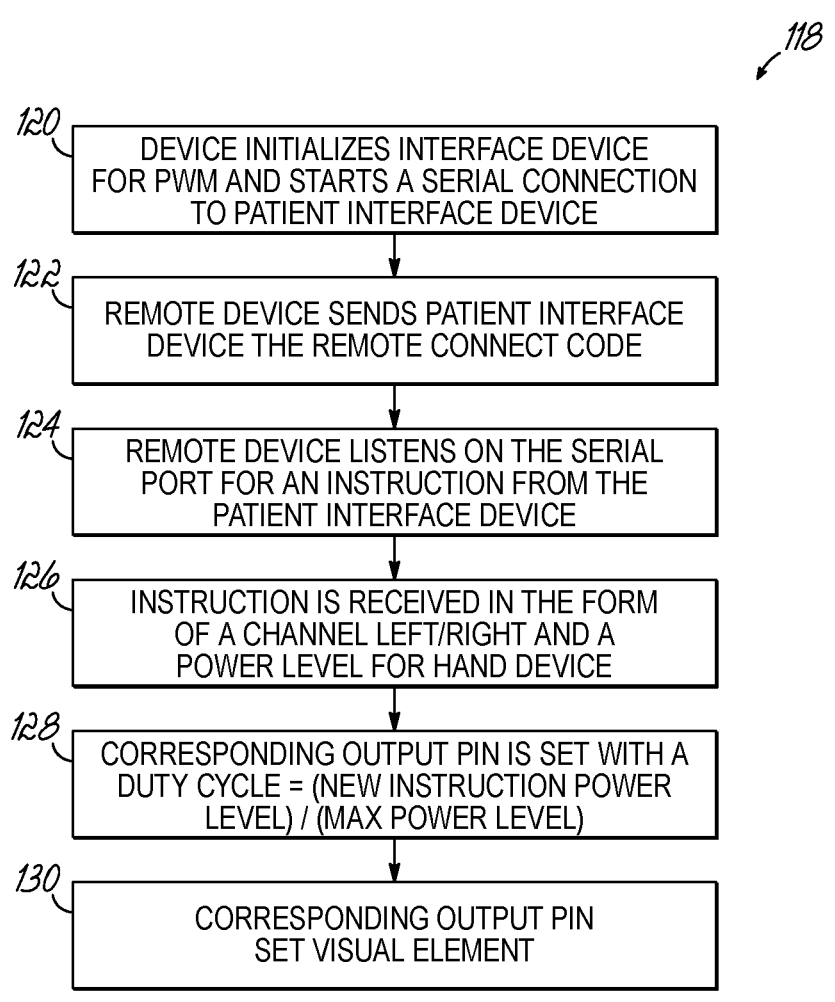

*118*

*120* DEVICE INITIALIZES INTERFACE DEVICE FOR PWM AND STARTS A SERIAL CONNECTION TO PATIENT INTERFACE DEVICE

*122* REMOTE DEVICE SENDS PATIENT INTERFACE DEVICE THE REMOTE CONNECT CODE

*124* REMOTE DEVICE LISTENS ON THE SERIAL PORT FOR AN INSTRUCTION FROM THE PATIENT INTERFACE DEVICE

*126* INSTRUCTION IS RECEIVED IN THE FORM OF A CHANNEL LEFT/RIGHT AND A POWER LEVEL FOR HAND DEVICE

*128* CORRESPONDING OUTPUT PIN IS SET WITH A DUTY CYCLE = (NEW INSTRUCTION POWER LEVEL) / (MAX POWER LEVEL)

*130* CORRESPONDING OUTPUT PIN SET VISUAL ELEMENT

FIG. 4

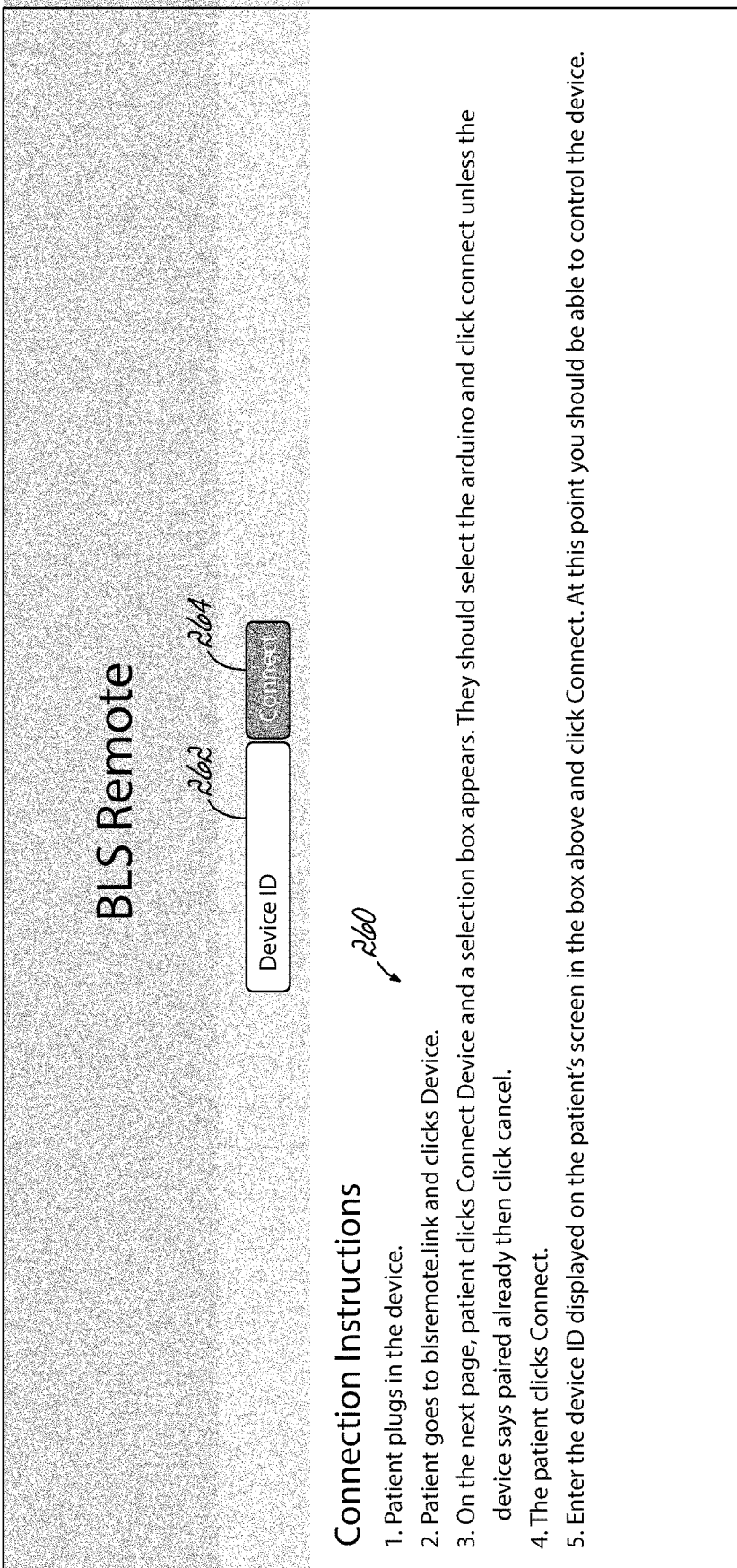

BLS Remote

Device ID

CONNECT

260

262

264

Connection Instructions

1. Patient plugs in the device.

2. Patient goes to blsremote.link and clicks Device.

3. On the next page, patient clicks Connect Device and a selection box appears. They should select the arduino and click connect unless the device says paired already then click cancel.

4. The patient clicks Connect.

5. Enter the device ID displayed on the patient's screen in the box above and click Connect. At this point you should be able to control the device.

DEVICE FOR INDUCING ALTERNATING TACTILE STIMULATIONS

CROSS-REFERENCE TO RELATED APPLICATIONS

This application claims the benefit of priority to U.S. Provisional Patent Application Ser. No. 63/086,879 filed Oct. 2, 2020 (pending), the disclosure of which is incorporated by reference herein in its entirety.

FIELD OF THE INVENTION

This application is related to eye movement desensitization and processing (EMDR) therapy and particularly to the delivery of stimulation therapy related thereto.

BACKGROUND OF THE INVENTION

Post-Traumatic Stress Disorder (PTSD) is related to the delayed response of a human being to one or more past traumatic experiences or visual events. PTSD is generally characterized by anxiety attacks, sleep disturbances, flashbacks, and other symptoms which relate to the prior traumatic event.

A form of therapy for treating PTSD is Eye Movement Desensitization and Reprocessing (EMDR). In EMDR, a therapist instructs a person being treated to recall distressing images from the traumatic event, to identify related negative thoughts/beliefs, and then to move their eyes rapidly back and forth. Such a therapy process in EMDR uses Bilateral Stimulation or BLS, wherein stimulation is presented to opposing sides of the body. The eye movement is one form of Bilateral Stimulation (BLS) that is used in the process, but such therapy has also grown to include other stimulation methodologies as well.

There are generally three BLS variations used for the EMDR procedure. The first variation is the procedure as stated above, using rapid eye movements. Another variation involves the use of soft, alternating audible tones. For example, a tone is played in the right ear, then the left ear, then the right ear, then left ear and so forth. Finally, the other significant stimulation variation involves the use of alternating tactile stimulation of the client's hands, for example, or possibly other bilateral body parts. All three of the EMDR procedure variations including rapid eye movements, alternating tones, and alternating tactile stimulations, appear to produce beneficial treatment effects.

One form of BLS involves having a patient grasp a pair of paddles, one in each hand, that then vibrate alternately for the bilateral stimulation. Clients tend to have a preference for one variation or another. For example, some clients prefer to process their traumatic memories with eyes closed (ruling out eye movements), and some prefer processing trauma in a quiet environment (ruling out alternating tones), and therefore the tactile stimulation is preferable. Sometimes the patients emotional state interferes with their ability to maintain rapid eye movements making it necessary to switch to tones or tactile stimulations in mid-session. Furthermore, children may have attention spans too short for processing trauma with eye movements, necessitating an alternative. Client handicaps, such as blindness or deafness, may also rule out one or more procedure variations. As such tactile stimulation, may be preferable in various situations, although the EMDR therapists need to be flexible and open to the varying needs and preferences of clients when deciding which variation to use at a given moment.

Generally, such therapy would be provided in person during a visit to a therapist or other care provider. As such, the therapy involves the use of a machine or system utilizing vibrating elements with possible other sound and visual elements for the EMDR procedure. Such a system is located in the therapist's office or some other facility and may be utilized when the patient is present with the therapist and system.

Accordingly, current EMDR procedures and systems are somewhat inconvenient as they require the patient to be local with both the therapist and the system. One such system is set forth in U.S. Pat. No. 6,001,073. Such a system is able to provide the desired tactile stimulation without a therapist touch. However, it suffers from a similar drawback of having to be local to both the therapist and patient. There may be times when a patient may need therapy but cannot be physically present. This has particularly been an issue wherein help for a remote patient is desired, such as with the recent COVID-19 pandemic. Social distancing is desired, and the patient may be prevented from being physically present with the therapist.

Accordingly, there are still needs within the area of EMDR therapy wherein such therapy may be offered in a more convenient manner for both the patient as well as the therapist. More specifically, it may be desirable in certain situations to be able to provide the therapy wherein the patient is not local with or is otherwise remote from the therapist and the therapist's equipment. Accordingly, the present invention addresses some of the needs in EMDR therapy and provides improved system for addressing the noted shortcomings in current therapy protocol.

SUMMARY OF THE INVENTION

A system for providing a therapy session between a therapist and a patient includes a therapist interface device that is configured for presenting a therapist user at a first location with a control interface to communicate with a remote patient interface device at a second location. The patient interface device is configured for presenting a patient user with a communication interface for communicating with the therapist interface device over a network. A stimulation device is located at the second location with the patient interface device and is configured for providing tactile stimulation to a patient user. In one embodiment, the stimulation device provides bilateral tactile stimulation. The stimulation device is configured for serially coupling with the patient interface device for receiving stimulation instructions from the patient interface device. The control interface of the therapist device is configured for receiving a control input from the therapist user that is reflective of a level of stimulation and a duration of stimulation to be delivered to a patient user. The patient interface device uses the control input to generate stimulation instructions to drive the stimulation device to provide tactile stimulation to the patient user based upon the control input.

BRIEF DESCRIPTION OF THE DRAWINGS

The accompanying drawings, which are incorporated in and constitute a part of this specification, illustrate embodiments of the invention and together with the detailed description given below, serve to explain various aspects of the invention.

FIG. 2 is a flow diagram of the connection between a therapist and patient for implementing a stimulation session in accordance with and embodiment of the invention.

FIG. 4 is a flow diagram of the control of a remote stimulation devices through a patient interface device for implementation of a stimulation session in accordance with an embodiment of the invention.

FIG. 7 is a schematic view of an exemplary website page for a therapist for implementing the tactile stimulation of the invention.

DETAILED DESCRIPTION OF EMBODIMENTS OF THE INVENTION

In accordance with one embodiment of the invention, a patient is provided with a remote system that may couple with a patient's computer or other computing device, such as a laptop or desktop computer. The system communicates as well with a therapist's device, such as another laptop or desktop computer, through a network. In one embodiment, a cloud network is utilized providing a dynamic database functionality for linking the therapist and patient, and also providing the therapist with control of the remote patient's device, such as control of vibrating paddles, audible features, and visual features of the system. The patient can thus be located remotely from the therapist and the therapist can provide the desired control for the EMDR therapy session conducted with the parties in different locations. The patient has the ability to initiate the therapy session and the therapist has the ability to adjust the patient's remote BLS devices during the remote session, such as to change the intensity of the stimulation as well as the frequency of the various bilateral stimulations, such as the duration of each stimulation on one side before switching to stimulation on the other side, for example.

Figure 1:
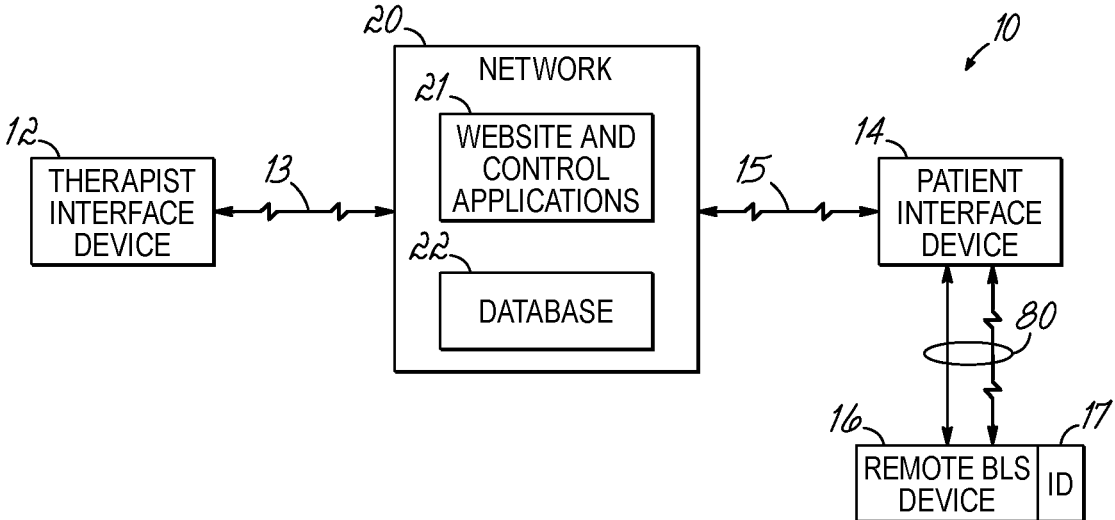
FIG. 1 is a block diagram of components of one embodiment for implementing the tactile stimulation of the invention.

FIG. 1 illustrates an overall schematic view of the system 10 of the invention in accordance with one embodiment. Specifically, a therapist interface device 12 and a patient interface device 14 are located geographically remote from each other and are coupled through a suitable network 20. Although the examples discuss remote patients and a therapist, the invention may still have applicability with the parties located together. For example, system 10 illustrated in FIG. 1 includes a therapist interface device 12 that is local to the therapist. The therapist interface device 12 and patient interface device 14 may each be a suitable computing device or computer, such as a laptop or desktop computer. However, a mobile device such as a telephone or tablet might also be utilized to provide the therapist and patient with a way to communicate in accordance with the invention. Hereinafter, such devices will be referred to as interface devices.

Similarly, the patient interface device 14 is located locally to the patient and generally remote from the therapist. Coupled with the patient interface device is a remote BLS stimulation device 16 that is used for implementing the various desired stimulation methods used in the therapy session. The patient physically interacts with the BLS device and therefore the patient needs physical access to the device. For example, the remote BLS device 16 may provide tactile stimulations, as well as possibly audible and visual stimulations to be perceived by a patient. In one of the exemplary embodiments as described hereinbelow, tactile stimulation is provided through the BLS device 16, and other stimulation such as audible or visual stimulation might be implemented through the patient interface device, as described. Each of the interface devices 12, 14 are coupled through an appropriately wired or wireless link 13, 15 with a suitable communication network. For example, in one embodiment, the network 20 might be a cloud network 20. In one embodiment of the invention, cloud services, through Amazon Web Services (AWS) is implemented incorporating a database 22, such as DynamoDB and includes a plurality of programs 21, such as a suitable API for providing access to the network from the various interface devices 12, 14. More specifically, the network 20 also runs one or more website programs 21 with suitable logic code for connecting the interface devices together that will post webpages for each of the therapist interface device 12 and patient interface device 14. The webpages provided through the network programs/applications 21 contain suitable code, such as JavaScript code, that connects each of the therapist and patient computers to the application logic 21 through an API, such as a WebSockets API Gateway. In that way, the patient and therapist may be in separate locations and the EDMR therapy session may be accomplished with the desired delivery of BLS to the patient in the therapy protocol.

To provide the connection between the therapist and patient for the delivery of patient BLS functions, the patient's remote BLS device 16 is utilized. As discussed below, the remote BLS device 16 includes the various stimulation components, such as elements for tactile stimulation. Optionally, the device 16 might also include visual stimulation and audible stimulation, or such additional, non-tactile stimulation might be handled through the interface device 14 as disclosed. The remote BLS device 16 includes ID information 17 that is associated with the particular remote BLS device 16. A therapist may oversee sessions with a plurality of different remote patients that will each have their own dedicated remote BLS device at their own specific geographic location. As such, each patient will have a unique ID for their remote BLS device that is used by the system 10 for managing the various patients. In accordance with one feature of the inventive system, the database 22 in the network 20 also contains the identification information 17 for all of the plurality of remote BLS devices 16 so that a therapist may interface with the plurality of different patients. The ID information 17 from the remote BLS device 16 is provided through the patient interface device 14 when a patient plugs the remote BLS device 16 into their interface device 14. Upon the patient connecting their remote BLS device, an entry is made into the database with the ID information. As discussed further herein, the therapist then connects utilizing the remote ID associated with the patient and patient remote BLS device 16 and the database is searched for this ID information 17. The database 22 contains the identification information of the various patients and, as a result of a search, returns session identification information for the patient, through the application 21. The session identification information is received by the therapist interface device 12 and is associated with the patient and the therapy for the patient. This connection then allows any control inputs from the therapist interface device 12 to be routed through the network 20 and directly to the remote patient's interface device 14. The patient's interface device 14 then uses the control inputs received from the therapist interface device 12 and updates the local control parameters of the patient remote BLS device 16 so that the proper control is provided for a therapy session.

Figure 8:
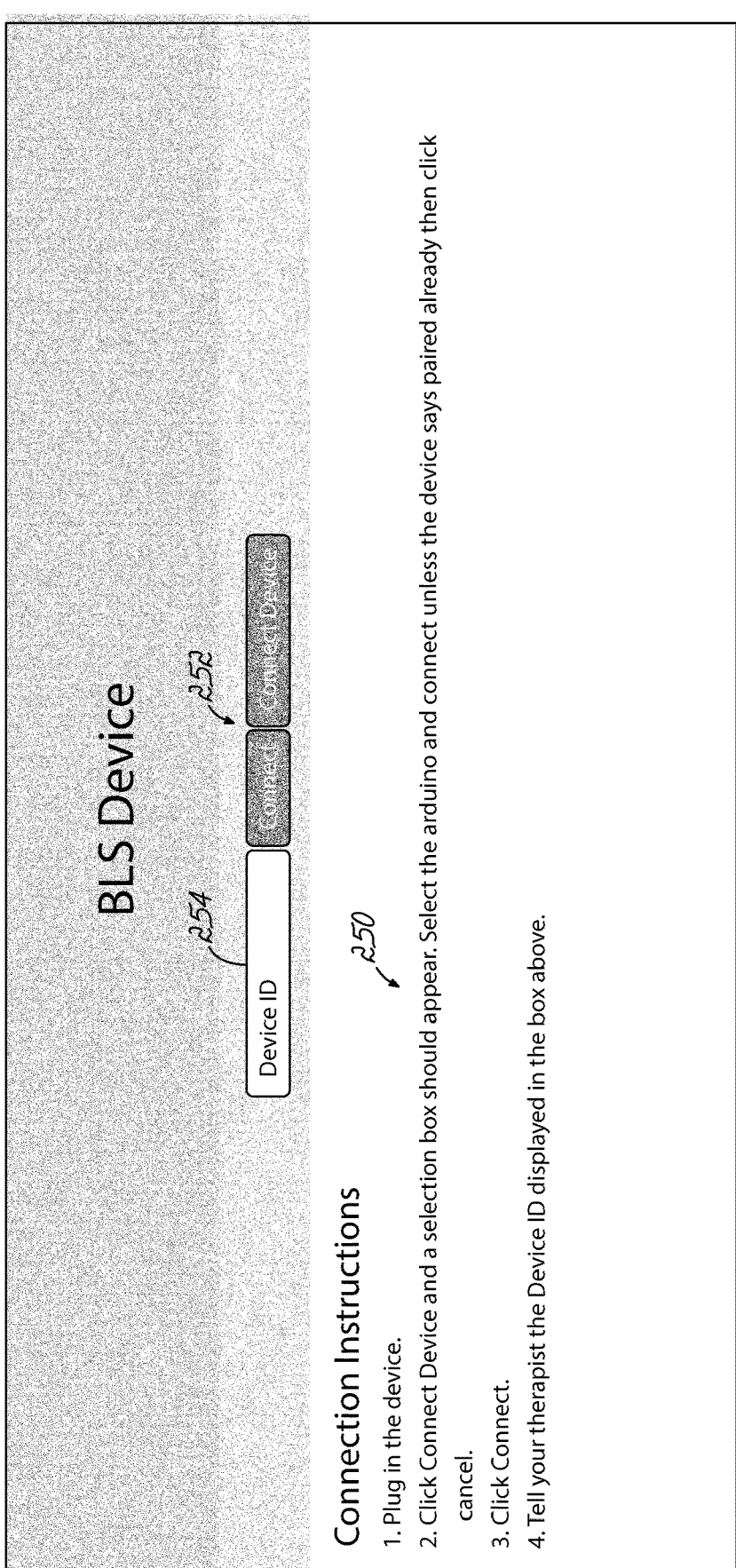
FIG. 8 is a schematic view of an exemplary website page for a patient for implementing the tactile stimulation of the invention.

More specifically, turning to FIG. 2, a linking process 40 is illustrated for linking the patient and providing the therapist with control of the patient's remote BLS device 16 for a therapy session. To initiate a session and link with the therapist, the patient goes to a website page provided by one or more applications 21 provided through the network 20 and plugs the remote BLS device 16 into their interface device 14. (Step 42). The website page might be from a static website, and as noted, the applications 21 host a static website page for each of the patient and therapist interface devices. The website page(s) contain Javascript code that runs on each of the devices 12, 14 and connects each of the patient and therapist devices 12, 14 to the network 20 through an appropriate interface. In one embodiment a Websockets API is provided and establishes a constant connection for a full-duplex therapist/patient communication through the network 20. A Websocket API endpoint (room) is opened when the patient plugs in their remote BLS device 16, as noted in step 44, and the database 22 is updated with the endpoint identification information/ID (information ID 17) for the endpoint. In other words, a remote connect code is generated by the application(s) 21 for making the patient/therapist connection based on the endpoint identification information/ID (information ID 17). For example, the serial number of the remote BLS device might be used in the remote connect code. The remote connect code for a session is then provided to the patient through their website page interface at device 14, which shows the connect code, as noted in step 46. For example, as disclosed herein, FIG. 8 shows an exemplary website page for a patient providing instructions 250 for connecting as well as selectable fields 252 for connecting in a session. The remote connect code (e.g., device ID) may be displayed in field 254.

For the therapist to connect with the patient, the therapist needs the unique remote connect code 254 generated by application(s) 21. To that end, as noted in step 48, the patient communicates the connect code to the therapist. In accordance with embodiments of the invention, this may be done in a number of ways. For example, a phone call or a text message may be made from the patient to the therapist to convey the connect code information. Alternatively, a video link might exist between the patient and therapist, such as through a Skype or Zoom link, or some other available video link and that link might be implemented to share the connect code with the therapist. As noted in step 50, the therapist then uses the connect code information and goes to their respective website page on the therapist interface device/computer 12 to provide the connect code in an appropriate input field. Through the therapist interface device 12 and the link 13 with network 20, the applications 21 implementing the invention search the database 22 to find the specific connect code therein as noted in step 52. The connect code information is linked with the WebSocket endpoint (room) information for a session initiated by the patient and that endpoint information is returned to the therapist interface device 12 as shown in step 54. The webpage interface of the therapist interface device 12 makes the WebSocket connection. FIG. 7 illustrates an exemplary website page for a therapist interface. It sets forth the instructions 260 for connecting in a session and provides a field 262 for entering a connect code (e.g., device ID). Further selectable fields 264 provide the connection where the session is to begin. Then the application(s) 21 send initialization messages to the patient's remote BLS device 16, through the patient interface device 14 (step 56). The applications 21 include the appropriate API for sending such control messages for control. The initialization messages include data for the control of remote BLS device 16. As discussed further herein, the remote BLS device 16 then sets new operational parameters and acknowledges the messages from the therapist website interface, as shown in step 58. At that point, both the therapist and patient are ready for a treatment session.

Figure 5:
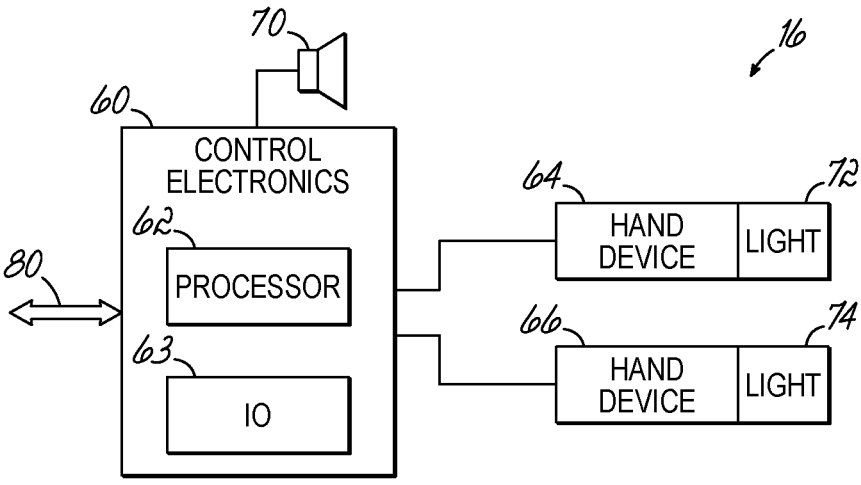
FIG. 5 is a block diagram of components of a stimulation device in accordance with one embodiment of the invention.

In accordance with one embodiment of the invention, the remote BLS device 16 primarily provides alternating and bilateral stimulation to a patient and incorporates two hand devices that each vibrate sequentially at a particular intensity and for a particular duration of time. To that end, referring to FIG. 5, an embodiment of the remote BLS device 16 is illustrated. The remote BLS device 16 incorporates control electronics 60 which includes a processor or processing circuit 62 for controlling the hand devices 64, 66, as well as other stimulation output devices in accordance with the invention. The hand devices 64, 66 may be grippable paddle devices which are held by a patient and incorporate suitable vibration motors therein (not shown) to vibrate the paddles for providing tactile stimulation. In one embodiment, the hand devices only include suitable structure for providing tactile stimulation. If additional stimulation is provided to accompany the tactile stimulation, it might be provided through the patient interface device, such as a laptop computer. For example, audible stimulation might be provided through the patient interface device 14 or through headphones plugged into the device 14. The volume might be set by the patient. Alternatively, the patient might be linked audibly with the therapist, such as in a conference call or other video format, such as a ZOOM call or Microsoft Teams Meetings call or Skype call and the therapist might provide audible stimulation through that connection. For example, the patient might hear that audible stimulation through the speaker of the interface device 14, such as a laptop, or through headphones plugged into the device 14. The therapist could then select the maximum and minimum audible sounds.

In accordance with another embodiment, the remote BLS device might have one or more speaker elements 70 that are utilized as well to provide left and right audible beeps. Such sounds might be controlled by the therapist, through the network in a similar way that the tactile stimulation is controlled as described herein. For example, the speaker elements 70 might be powered to provide an audible sound, such as a beep that has a particular volume as well as a particular duration to the left and right side of a patient in combination with tactile stimulation.

In another embodiment of the invention, visual stimulation might be implemented in addition to tactile stimulation. For example, as noted, the patient might be linked visually with the therapist, such as video call, such as a ZOOM call or Microsoft Teams Meetings call or Skype call and the therapist might provide visual stimulation through that connection. For example, from the screen of the therapist, visual cues that are synchronized with the tactile stimulation might be provided.

In still another embodiment, the remote BLS device 16 interfaced with the therapist and device 12 in a similar way may incorporate light elements 72, 74 which may be utilized in the therapy as well to provide left and right visual stimulation along with the vibration of the hard devices 64, 66. The light devices 72, 74 may alternately flash back and forth, such as from side-to-side on the remote BLS device 16 to provide visual bilateral stimulation. The light elements might be controlled in a similar fashion as the tactile stimulation and synchronized with the tactile stimulation. Or a separate visual stimulation device or accessory might be plugged into the interface device 14 similar to the BLS device 16 and may provide visual stimulation in that way.

In one embodiment, for tactile stimulation each of the hand devices 64, 66 will be selectively powered to provide a particular intensity of vibration for a particular duration of time at each of a left and right device. As may be appreciated, the remote BLS device will have a suitable housing for containing the processor 62 as well as other circuitry necessary for powering and/or operating the hand devices 64, 66 as well as any optional speaker(s) 70 or light devices 72, 74. Remote BLS device 16 will incorporate suitable input/output circuitry 63, such as for plugging in the hand devices 64, 66. In one embodiment, a three-ring connector is utilized to plug the hand devices/paddles 64, 66 into the processing circuitry 60 of the remote BLS device. Remote BLS device 16 will be connected to the patient interface device with one or more wired or wireless connections 80. For example, the device 16 might be plugged into the patient interface device 14, such as through a USB plug or connection, for providing a serial link for serial commands and signals to the remote BLS device 16. Alternatively, a wireless serial connection between the remote BLS device 16 and the patient interface device/computer 14, such as a Bluetooth link, may also be utilized as shown in FIG. 1.

Figure 9:
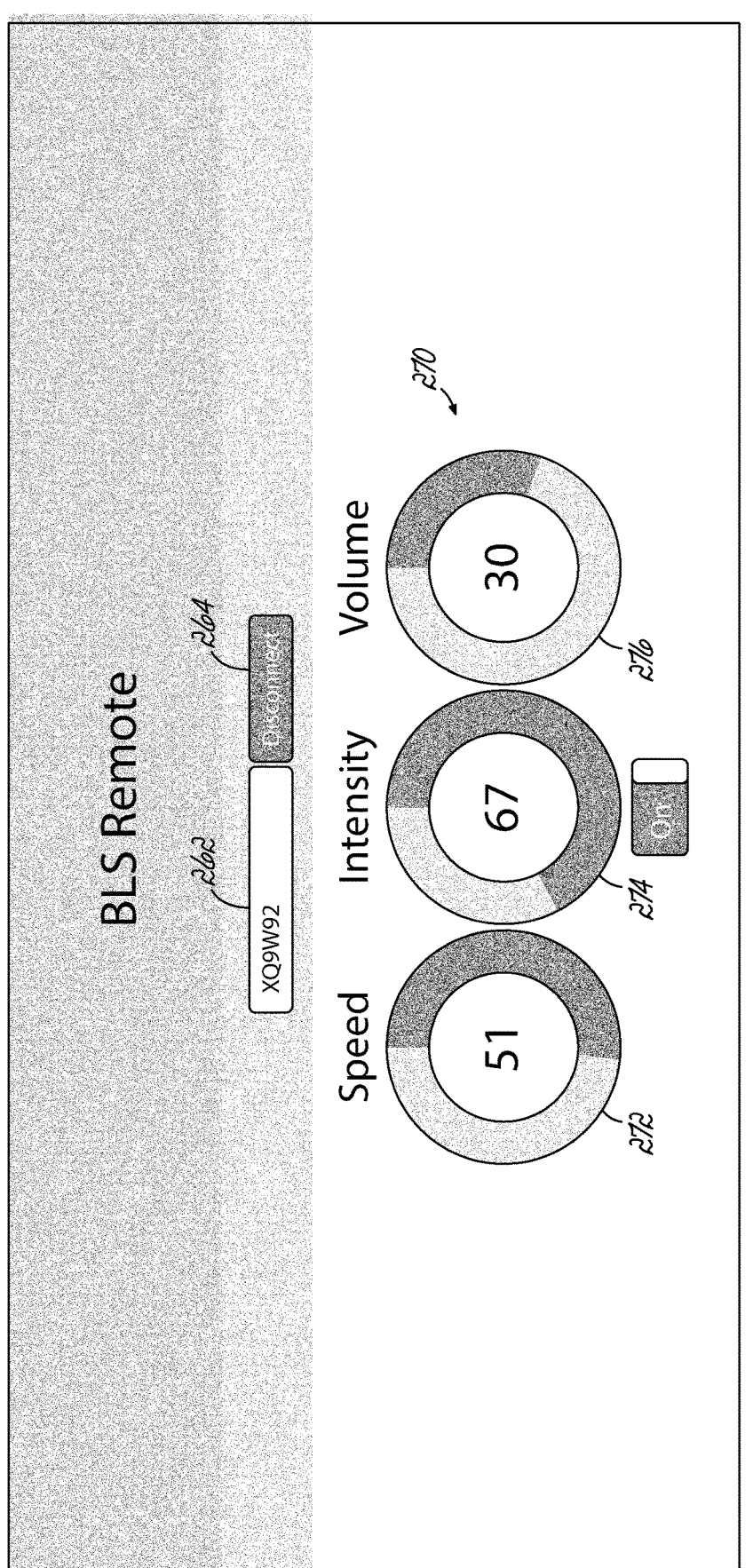
FIG. 9 is a schematic view of another exemplary website page for a therapist for adjusting the tactile stimulation of the invention.

The therapist has control of remote BLS device 16 through a link with the patient interface device 14 through network 20. To that end, the therapist interfaces with interface device 12 and provides the appropriate settings for the operation of the remote BLS device 16 and the implementation and control of a therapy session through the system 10 of the invention. For example, referring to FIG. 9, the therapist website page presents a number of selectable fields for controlling the remote device 16 once a session has begun and the therapist is coupled to the device 16. For example, field 272 allows selection of the speed of the stimulation on a 0-100%. This is reflected in the duration of the particular tactile stimulation. Field 274 allows selection of the stimulation intensity on a similar scale, while field 276 provides for volume adjustment on a 0-100% scale. Other parameters might be set by a therapist in accordance with the invention.

Figure 3:
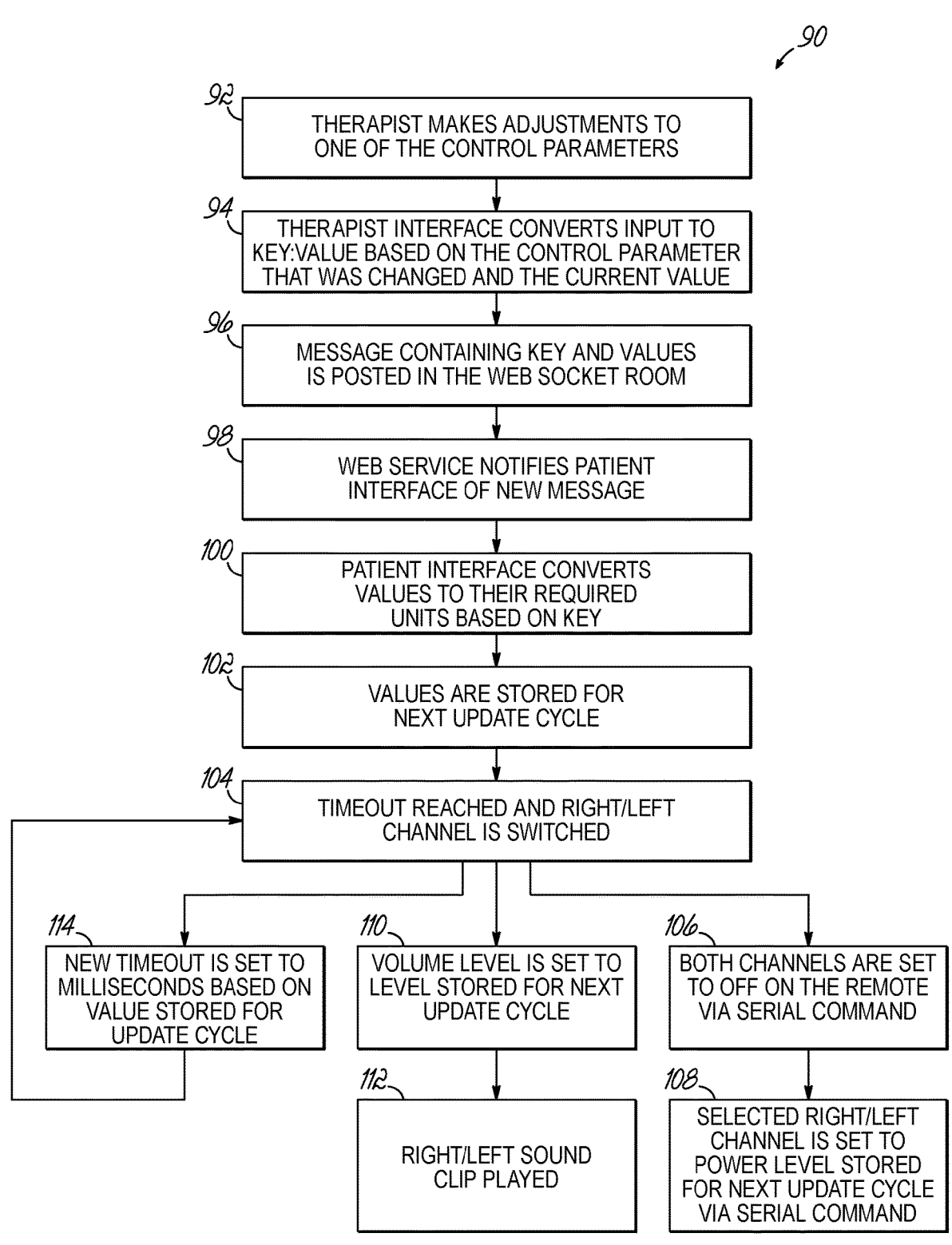
FIG. 3 is a flow diagram of the control by a therapist of remote stimulation devices for implementation of a stimulation session in accordance with an embodiment of the invention.

In accordance with an embodiment of the invention, system 10 is utilized for providing bilateral stimulation to a patient, including the use of tactile external stimuli, through the hand devices 64, 66 for rhythmic, side-to-side stimulation. As noted, with embodiments of the invention, visual stimulation may also be included, including the side-to-side utilization of lights 72, 74 and/or audible sounds, such as audible beeps. The therapist can make adjustments to the remote BLS device 16 to control the operation of the various stimulation elements and modes pursuant to a therapy session. Referring to FIG. 3, a flowchart sets forth the various steps and operations of the system 10 for controlling remote BLS device 16 for a therapy session.

Specifically, flowchart 90 sets forth the program flow in accordance with the invention for a therapist to make adjustments to one or more of the control parameters for remote BLS device 16. (Step 92). For example, the therapist, through their interface device 12 and the web interface program/logic running on the device may, for example, set forth a particular intensity for the vibration or tactile stimulation of the hand devices 64, 66 (see FIG. 9). Also, the duration of the alternating tactile stimulation, pursuant to the bilateral stimulation aspects, might also be set by the therapist through programs 214 running on device 12 (see FIG. 9). Other parameters, such as the volume and duration of one or more speakers and/or the duration and control of the lights might also be input by the therapist if that is an option (see FIG. 9).

In one embodiment, such input might be made manually so that manual adjustment to one of the controls parameters of the remote BLS device 16 is affected. Alternatively, a number of different preset control parameters might be provided for selection through the applications 214 of device 12 that provide interaction with the patient and also the hardware control for controlling the BLS device 16. In that way, the therapist can select a certain preset group of control parameters for the remote BLS device. As an example, the therapist may have had several therapy sessions with a patient. In one embodiment of the invention, the application 21 and database 22 allow the therapist to save data associated with one or more therapy sessions. The therapist may then select a stored set of control parameters through the network application 21 reflective of earlier therapy sessions. Still further, in another embodiment, the application 21/database 22 may include a plurality of stored sets of control parameters that may be selected by the therapist for use with a patient. Such stored sets may be based on particular patients or conditions of the therapy session. For example, there may be a regular set of control parameters that the therapist may select to provide a basic therapy session. Alternatively, if there are distractions for the patient, there may be a selectable set of control parameters that may be associated with a distracted condition in the therapy session. As may be appreciated, other conditions may be addressed by stored sets of control parameters that might be selected by the therapist in a session with a patient. For example, various selectable sets of stored control parameters might be stored on the database. Once control parameters are selected manually or with a stored or preset group of control parameters, the program 21 converts the inputs to a key:value pair set or string that is based on the control parameter that was changed as well as the current value for that parameter. (Step 94). The key:value set may be stored as set forth herein for future use. A message containing the key:value set is then posted to the WebSocket room of the network 20 that is associated with the therapy session. (Step 96). Then, the application 21 notifies the patient interface program 214 running at interface device 14 that there is a new message for the patient. For example, the interface to the patient implemented through the patient web interface and logic 214 and an API built into the patient browser provides such a connection and notification (Step 98)

The patient interface program 214 then converts the entered values to their required units based on the key. (Step 100). The units are reflective of the inputs needed to control remote BLS device 16 and the data is serialized. For example, if the intensity of the tactile stimulation is changed from 50% to 75%, the serialized data will reflect that the intensity tactile stimulation is to be changed and that the new value is 75%. According to step 102, the control values are stored for use by the patient interface device 14 and will be used for the next update cycle to the remote BLS device 16.

(Step 102). For example, when a patient session (and room) is opened as described, the application 21 maintains a history that is kept in database 22. Such history may be lost when the session is closed or might be stored in database 22 to be retrieved at a later time. Alternatively such values might be stored on the patent interface device 14.

The remote BLS device works based upon an update cycle or a "tick" or an interrupt based update that occurs when an interval associated with the update cycle times out. The update cycle is set by the program 21 which provides the interface between the therapist device 12 and patient device 14 and controls the BLS device 16. In one embodiment of the invention, the timeout for the update cycle for remote BLS device 16 is associated with or tied to the switching of signals between the hand devices 64, 66 of device 16. A switching occurs wherein the right and left channels associated with the right and left hand devices 64, 66 and the stimulation they provide are switched. That is, during a therapy session, each time that a switching timeout or duration timeout is reached, the right and left channel is switched as set forth in step 104 and a number of other update actions take place through remote BLS device 16.

Referring again to FIG. 3, when the timeout of a duration or a "tick" is reached or there is an update, and channels are switched between the hand devices, both channels of the respective hand devices are initially set to an OFF position by the remote BLS device 16 via a serial command from the patient interface device 14 through connection 80. (Step 106). Then, a command is sent serially to the remote BLS device 16 based upon the stored power level or value for the next update cycle per step 108. The selected hand device 64, 66 is then powered appropriately for providing stimulation at the commanded power level or intensity. (Step 108). The tactile stimulation is provided to the patient for a duration set by the therapist until the stimulation times out (considered a "tick"). A stimulation control is provided by program 21 for other BLS stimulation modes.

Simultaneously, a volume level for any audible stimulation that is available through device 16 through speaker 70 or through the patient interface device 14 might be set for the level that was stored for the next update cycle per step 102. (Step 110). Then, an appropriate right or left sound clip is played in combination with the right or left hand device stimulation. (Step 112). Alternately, or in addition to the tactile stimulation, a visual stimulation, such as the illumination of lights 72, 74 may occur either through patient interface device 14 or device 16 synchronized with the tactile stimulation or the duration set as a control parameter for the BLS process.

Additionally, upon a timeout or "tick", a new timeout value for the switching timeout or "tick" is set, such as in milliseconds, based upon the value stored for the update cycle. (Step 114) That is, the therapist can make adjustments to the control parameters and those parameters are provided to the patient interface device 14 where they are accessed and then implemented in each update cycle, upon the timeout of the previous cycle associated with the current right or left stimulation. Each time the stimulation is switched to the next hand device 64, 66 the current control parameters are utilized for tactile stimulation, as well as audible stimulation and/or visual stimulation and also the new timeout value is set for the next stimulation cycle. In that way, updates are provided with each timeout or switch of stimulation or each "tick". As appreciated, there may be no changes to the levels and values, and various cycles or ticks can progress with the same values.

In accordance with one aspect of the invention, the remote BLS device 16 interfaces with the patient interface device 14 through serial connection 80. Referring to FIG. 4, upon plugging in or connecting the remote BLS device 16 with interface device 14, through either a wired connection, such as a USB connection or wireless connection, the remote device initializes itself and starts a serial connection with the patient's interface device 14. The remote BLS device 16 also sets the output components, such as output pins to receive information and command protocols from the patient interface device 14, such as for example regarding the intensity for the tactile stimulation.

For example, in one embodiment of the invention as set forth in program flow 118 and step 120 in FIG. 4, the BLS device 16 initializes itself for receiving pulse width modulation (PWM) information reflective of the intensity tactile stimulation intensity to control motor components or other components of the BLS device 16 and starts the serial connection with the patient interface device. For example, through pulse width modulation, the tactile stimulation intensity level may be set, such as to 50% or 75% etc. In step 122, the remote BLS device sends a remote connect code to the patient interface device 14. For example, the remote BLS device might forward a serial number or other data regarding the identification of the remote BLS device. (Step 122) As noted, the remote connect code is used to provide a proper communication link between the remote BLS device and the patient interface device and also may be provided to the therapist interface device in order to provide the control of the remote BLS device to the therapist for a particular session using particular stimulus through the BLS device. Web interface/logic program of the patient interface device establishes the communication link between the patient interface device and the remote BLS device for passing the control instructions from the patient interface device to the remote BLS device. Next, the remote BLS device listens on the serial port of the connection 80 for an instruction from the patient interface device 14 as shown in step 124. An instruction is then received from the patient interface device 14 in the form of a stimulation channel command and a power or intensity level for the stimulation. For example, a channel left or right command is received as well as the selected power level set by the therapist either manually or through control parameters for the desired therapy session. Such channel commands might refer to the tactile stimulation or other stimulation (audible, visual) including which side of the bilateral stimulation and what intensity of vibration (or volume, intensity, etc.) (Step 126) The output pins to the remote BLS device for the various hand devices 64, 66 are then set with the appropriate duty cycle to achieve the selected power or intensity level of stimulation. The duty cycle is essentially the newly instructed power level as a ratio over the maximum power level of stimulation that can be provided to the hand devices 64, 60. For example, a 50% duty cycle or 75% duty cycle or some other duty cycle may be selected and provided at the corresponding output pins in each of the hand devices. Similar other commands are implemented, such as for the visual or audible elements through corresponding output pins based upon the selected left or right channel for the hand devices. To that end, the stimulation of the hand devices is provided. As noted herein, the tactile stimulation may be accompanied by appropriate illumination or sound, such as through the interface device 14 or through the light devices or elements 72, 74 or audible sounds from speakers 70.

Figure 6:
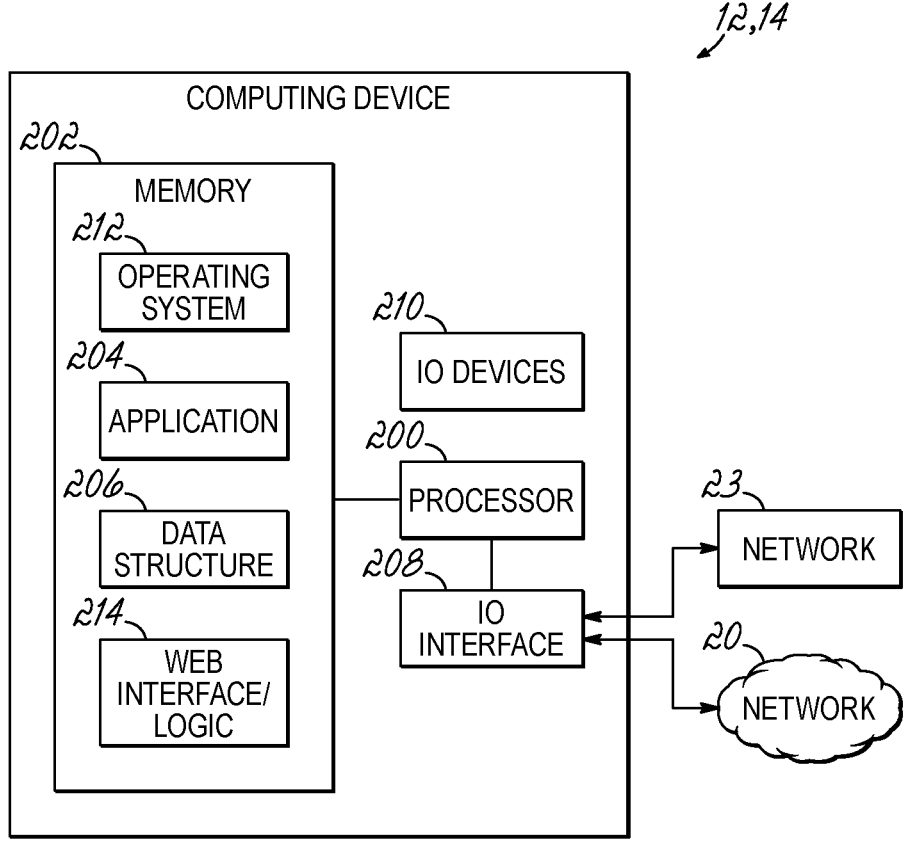
FIG. 6 is a block diagram of components of exemplary therapist and/or patient interface devices for implementing the tactile stimulation of the invention.

FIG. 6 provides an exemplary block diagram that illustrates the components of an exemplary device or system for implementing the therapist or patient interface device or computer 12, 14 consistent with embodiments of the invention. Generally, the interface devices 12, 14 are part of a system 10 of the invention for use by a therapist or patient. In one embodiment, the interface devices could be computing or computers, such as a laptop or desktop computer. Alternatively, the devices could be mobile devices, such as a tablet or phone device. The devices 12, 14 would include at least one processor element or processor 200 including at least one hardware-based microprocessor and a memory 202 coupled to the at least one processor 200. The memory 202 may represent the random access memory (RAM) devices comprising the main storage of the devices 12, 14 as well as any supplemental levels of memory, e.g., cache memories, non-volatile or backup memories (e.g., programmable or flash memories), read-only memories, etc. In addition, memory 202 may be considered to include memory storage physically located elsewhere in the devices, e.g., any cache memory in a microprocessor, as well as any storage capacity used as a virtual memory, e.g., as stored on a mass storage device or on another computing device coupled to the devices 12, 14. As described above with respect to the service system 10 of FIG. 1, the devices 12, 14 may include one or more appropriate applications 204 and data structures 206, and programs 214, such as web based applications and appropriate data, for interfacing through the network with a user for the purposes of a therapy session as described herein. For communication between the therapist and user devices, one or more appropriate input/output (IO) interface (s) 208 might be used for communication over the network 20, such as a cloud network, or other communication network 23. Generally, devices 12, 14 with include suitable input and output (IO) devices 210 and related hardware/software for receiving data/information from a user and displaying data/information to the user. For example, with a device 12, 14, the IO devices might include hardware components such as a keyboard, microphone, speaker, touch screen, display screen etc. and appropriate interface software for communicating or interfacing with a user. The IO interface 208 provides the hardware/software interface suitable for communication with other computing devices through the cloud 20 or other network 23. For example, such an IO interface may also include a cellular network interface, as well as a wireless or Wi-Fi interface or other suitable network in.

The devices 12, 14 typically operate under the control of an operating system 212 and/or application and will execute or otherwise rely upon various computer software applications, components, programs, objects, modules, data structures, etc. For example, a web application or interface/logic application 214 in accordance with the invention might run on the devices to allow for the therapist to control a therapy session or a patient to engage and initiate a therapy session as described herein. For example, the application 214 on a therapist interface device 12, such as javascript code, provides an interface to an appropriate API that provides the link to the network application 21 and to the patient interface device 14 for the creation of a session. The application 214 also provides the display of the selectable controls for controlling the tactile stimulation. On the patient interface device 14, the counterpart application 214 runs similar code, such as javascript code, to create and maintain the same interface to an appropriate API that provides the link to the network application 21 and therapist device 12. The application 214 on the patient device also runs the logic code for creating the timing features for the stimulation as discussed and also for sending signals to the BLS device to switch stimulation back and forth at the appropriate intensity or level. More specifically, the application 214 sends an appropriate control message to the remote BLS device regarding the particular vibration parameters and duration and then the remote BLS device sends the appropriate voltage pulses to the paddles or hand devices 64, 66 for stimulation.

A person having ordinary skill in the art will recognize that the environments illustrated in FIGS. 1 6 are not intended to limit the scope of embodiments of the invention. In particular, the components 12, 14 and 16 may include fewer or additional components consistent with alternative embodiments of the invention.

Indeed, a person having skill in the art will recognize that other alternative hardware and/or software environments may be used without departing from the scope of the invention. Additionally, a person having ordinary skill in the art will appreciate that the various devices or computing systems may include more or fewer applications configured therein. As such, other alternative hardware and software environments may be used in accordance with the operation of the invention without departing from the scope of embodiments of the invention interfaces for communication over network 20 or other network(s) 23.

The routines executed to implement the embodiments of the invention, whether implemented as part of an operating system or a specific application, component, program, object, module or sequence of instructions executed by one or more devices/controllers and/or control systems/computing systems are referred to herein as "applications" or "logic" or "code" The program or application code typically comprises one or more instructions that are resident at various times in various memory and storage devices in a controller and/or computing system, and that, when read and executed by one or more CPUs and/or of the respective controllers and/or computing system, cause that controller and/or computing system to perform the steps necessary to execute steps, elements, and/or blocks embodying the various aspects of the invention.

In addition, various program code described hereinabove or hereinafter may be identified based upon the application or software component within which it is implemented in a specific embodiment of the invention. However, it should be appreciated that any particular program nomenclature is used merely for convenience, and thus the invention should not be limited to use solely in any specific application identified and/or implied by such nomenclature. Furthermore, given the typically endless number of manners in which computer programs may be organized into routines, procedures, methods, modules, objects, and the like, as well as the various manners in which program functionality may be allocated among various software layers that are resident within a typical computer (e.g., operating systems, libraries, APIs, applications, applets, etc.), it should be appreciated that the invention is not limited to the specific organization and allocation of program functionality described herein.

While the present invention has been illustrated by a description of various embodiments and while these embodiments have been described in some detail, it is not the intention of the inventors to restrict or in any way limit the scope of the appended claims to such detail. Thus, additional advantages and modifications will readily appear to those of ordinary skill in the art. The various features of the invention may be used alone or in any combination depending on the needs and preferences of the user.

What is claimed is:

1. A system for providing a therapy session between a therapist and a patient comprising:

a therapist interface device, the therapist interface device configured for presenting a therapist user at a first location with a control interface;

a patient interface device, the patient interface device configured for presenting a patient user at a second location, remote from the first location, a communication interface for communicating with the therapist interface device over a network;

a stimulation device storing a unique identification, and configured for providing tactile stimulation to the patient user, the stimulation device configured for serially coupling with the patient interface device for receiving stimulation instructions from the patient interface device;

a control application and database coupled with the therapist interface device and patient interface device, the control application configured for controlling a therapy session, the database including a plurality of stored sets of control parameters for a therapy session;

wherein:

the control interface of the therapist interface device is configured for receiving a control input from the therapist user for selecting at least one stored set of control parameters stimulation through a control application reflective for use in a therapy session, the control parameters including a level of stimulation and a duration of stimulation to be delivered to the patient user, the patient interface device configured for receiving and storing the set of control parameters including the level and duration of stimulation from the control interface, using the stored set of control parameters control input to generate stimulation instructions to drive the stimulation device to provide tactile stimulation to the patient user based upon the control input;

the patient interface device initiates a session with the therapist interface device by updating the database with the unique identification after a connection is established between the patient interface device and the stimulation device, and the control application generates a remote connect code including the unique identification, which is sent to the patient interface device;

wherein the stimulation device is further configured for providing alternating bilateral tactile stimulation between two stimulation elements configured to be coupled to each lateral side of the patient user, the control input providing a level of stimulation for each stimulation element and a duration of stimulation delivered to the patient user for one element before switching to provide stimulation with the other element;

wherein a switching timeout for an update cycle for the stimulation device is associated with or tied to switching of signals between the stimulation elements and the switching occurs based on right and left channels associated with the respective stimulation elements and the stimulation they provide are switched; and wherein during the therapy session, each time that the switching timeout is reached, the right and left channel is switched in a manner that update actions take place through the stimulation device; and wherein the tactile stimulation to the patient user is applied in a series of update cycles, based on the therapist user making adjustments to the control parameters, the control application is configured for implementing the adjustments in a next successive update cycle from an adjustment after a previous update cycle.

2. The system of claim 1 further including a device for providing at least one of audible stimulation or visual stimulation.

3. The system of claim 2, wherein the patient interface device provides the at least one audible stimulation or visual stimulation.

4. The system of claim 2, wherein the stimulation device provides the at least one audible stimulation or visual stimulation.

5. The system of claim 1, wherein the stored set of control parameters are based on at least one of the patient or conditions of the therapy session.

6. The system of claim 1, wherein the control application maintains a history of a therapy session that is stored in the database.

7. A system for providing a therapy session between a therapist and a patient comprising:

a therapist interface device, the therapist interface device configured for presenting a therapist user at a first location with a control interface;

a patient interface device, the patient interface device configured for presenting a patient user at a second location, remote from the first location, a communication interface for communicating with the therapist interface device over a network;

a stimulation device storing a unique identification, and configured for providing tactile stimulation to the patient user, the stimulation device configured for serially coupling with the patient interface device for receiving stimulation instructions from the patient interface device;

a control application and database coupled with the therapist interface device and patient interface device, the control application configured for controlling a therapy session, the database including a plurality of stored sets of control parameters for a therapy session;

wherein:

the control interface of the therapist interface device is configured for receiving a control input from the therapist user for selecting at least one stored set of control parameters stimulation through a control application reflective for use in a therapy session, the control parameters including a level of stimulation and a duration of stimulation to be delivered to the patient user, the patient interface device configured for receiving and storing the set of control parameters including the level and duration of stimulation from the control interface, using the stored set of control parameters control input to generate stimulation instructions to drive the stimulation device to provide tactile stimulation to the patient user based upon the control input;

the patient interface device initiates a session with the therapist interface device by updating the database with the unique identification after a connection is established between the patient interface device and the stimulation device, and the control application generates a remote connect code including the unique identification, which is sent to the patient interface device;

wherein the stimulation device is further configured for providing alternating bilateral tactile stimulation between a right stimulation element and a left stimulation element configured to be coupled to respective lateral side of the patient user, the control input providing a level of stimulation for each stimulation element and a duration of stimulation delivered to the patient user for one element before switching to provide stimulation with the other element;

wherein a switching timeout for an update cycle for the stimulation device is associated with or tied to switching of signals between the right stimulation element and the left stimulation element and the switching occurs based on right and left channels associated with the right stimulation element and the left stimulation element and the stimulation they provide are switched; and wherein during the therapy session, each time that the switching timeout is reached, the right and left channel is switched in a manner that update actions take place through the stimulation device; and wherein the tactile stimulation to the patient user is applied in a series of update cycles, based on the therapist user making adjustments to the control parameters, the control application is configured for implementing the adjustments in a next successive update cycle from an adjustment after a previous update cycle.

8. A system for providing a therapy session between a therapist and a patient comprising:

a therapist interface device, the therapist interface device configured for presenting a therapist user at a first location with a control interface;

a patient interface device, the patient interface device configured for presenting a patient user at a second location, remote from the first location, a communication interface for communicating with the therapist interface device over a network;

a stimulation device storing a unique identification, and configured for providing tactile stimulation to the patient user, the stimulation device configured for serially coupling with the patient interface device for receiving stimulation instructions from the patient interface device;

a control application and database coupled with the therapist interface device and patient interface device, the control application configured for controlling a therapy session, the database including a plurality of stored sets of control parameters for a therapy session;

wherein:

the control interface of the therapist interface device is configured for receiving a control input from the therapist user for selecting at least one stored set of control parameters stimulation through a control application reflective for use in a therapy session, the control parameters including a level of stimulation and a duration of stimulation to be delivered to the patient user, the patient interface device configured for receiving and storing the set of control parameters including the level and duration of stimulation from the control interface, using the stored set of control parameters control input to generate stimulation instructions to drive the stimulation device to provide tactile stimulation to the patient user based upon the control input;

the patient interface device initiates a session with the therapist interface device by updating the database with the unique identification after a connection is established between the patient interface device and the stimulation device, and the control application generates a remote connect code including the unique identification, which is sent to the patient interface device;

wherein the stimulation device is further configured for providing alternating bilateral tactile stimulation between a right hand-held stimulation element and a left hand-held stimulation element, the control input providing a level of stimulation for each stimulation element and a duration of stimulation delivered to the patient user for one element before switching to provide stimulation with the other element;

wherein a switching timeout for an update cycle for the stimulation device is associated with or tied to switching of signals between the right hand-held stimulation element and the left hand-held stimulation element and the switching occurs based on right and left channels associated with the right hand-held stimulation element and the left hand-held stimulation element and the stimulation they provide are switched; and wherein during the therapy session, each time that the switching timeout is reached, the right and left channel is switched in a manner that update actions take place through the stimulation device; and wherein the tactile stimulation to the patient user is applied in a series of update cycles, based on the therapist user making adjustments to the control parameters, the control application is configured for implementing the adjustments in a next successive update cycle from an adjustment after a previous update cycle.

* * * * *